United States Patent

Seidel et al.

[11] Patent Number: 5,306,398
[45] Date of Patent: Apr. 26, 1994

[54] PROCESS FOR THE PURIFICATION OF WASTE ACETIC ACID

[75] Inventors: Andreas Seidel, Cologne; Alfred Hauser, Erftstadt; Erhard Jägers, Bornheim, all of Fed. Rep. of Germany

[73] Assignee: Hoechst Aktiengesellschaft, Frankfurt am Main, Fed. Rep. of Germany

[21] Appl. No.: 978,905

[22] Filed: Nov. 19, 1992

[30] Foreign Application Priority Data

Dec. 5, 1991 [DE] Fed. Rep. of Germany ....... 4140082

[51] Int. Cl.$^5$ .......................... B01D 3/34; C07C 51/44
[52] U.S. Cl. ........................................ 203/33; 203/37; 203/71; 562/608
[58] Field of Search ............... 203/33, 36, 6, 37, 16, 203/60, 71; 562/608

[56] References Cited

U.S. PATENT DOCUMENTS

| | | | |
|---|---|---|---|
| 3,084,109 | 4/1963 | Reid et al. | 203/33 |
| 3,709,795 | 1/1973 | Singleton | 203/33 |
| 3,772,156 | 11/1973 | Johnson et al. | 203/33 |
| 3,864,418 | 2/1975 | Hughes et al. | 210/634 |
| 4,061,546 | 12/1977 | Singleton | 203/31 |
| 4,227,971 | 10/1980 | Zimmerschied | 203/33 |
| 4,384,924 | 5/1983 | Thoma | 203/33 |
| 4,898,644 | 2/1990 | Van Horn | 203/33 |

FOREIGN PATENT DOCUMENTS 1911032 10/1969 Fed. Rep. of Germany ........ 203/33
2423079 10/1982 Fed. Rep. of Germany .

*Primary Examiner*—Virginia Manoharan
*Attorney, Agent, or Firm*—Connolly & Hutz

[57] ABSTRACT

Waste acetic acid, which is contaminated by nitrogen compounds and also by hardly hydrolyzable halogen compounds, is purified by adding a complex-forming metal or one of the compounds thereof and a basic compound. The resultant mixture is kept at a temperature between 25° and 118° C. over a period of time of 1 to 6 hours. Finally, purified acetic acid is removed from the mixture by distilling.

1 Claim, No Drawings

PROCESS FOR THE PURIFICATION OF WASTE ACETIC ACID

The invention relates to a process for the purification of acetic acid, which is produced as a waste product of pharmaceuticals and contains, as impurities, nitrogen compounds, for example N-alkyl substituted ureas or amides, N,N-substituted 1,2-ethylenediamine, cyanocarboxylic acid and halogen compounds such as acetyl halides, hydrogen halide or mono-, di- and trichloroacetic acid.

An oxidative purification method for acetic acid is described in U.S. Pat. No. 4 061 546.

A process for working up acetic anhydride-containing waste acetic acid is described in DE-C 24 23 079. The purification of this waste acetic acid is carried out by a distillation, following previous hydrolysis of the anhydride fraction by addition of aqueous alkali metal acetates or hydroxide or alkaline earth metal acetates or hydroxide. In this purification method, nitrile and acetyl halide are also hydrolyzed and are enriched in the distillation pot.

However, these known purification methods fail in the case of the initially listed nitrogen compounds and hardly hydrolyzable halogen compounds.

Surprisingly, it has now been found that these nitrogen compounds and halogen compounds can be removed from the waste acetic acid by distillation, if in a first stage a complex-forming metal or one of the compounds thereof and a basic compound are added to the waste acetic acid and this mixture is kept at a temperature between 25° and 118° C. over a time period of 1 to 6 hours, in a second stage first runnings are distilled off and in a third stage purified acetic acid is distilled off, as overhead product, from a poorly volatile still residue.

The process according to the invention can, optionally, be developed in such a way that
a) the complex-forming metal used is iron, cobalt, nickel or copper or their compounds in the form of acetates, oxides or hydroxides;
b) the basic compound used is a compound selected from the group comprising hydroxides, hydrogen carbonates, carbonates or acetates of sodium, of potassium, of magnesium or of calcium;
c) a 1 to 100 molar excess of metal or metal compound is added, relative to the molar amount of the nitrogen compound and halogen compound contained in the waste acetic acid;
d) 1 to 10 parts by weight of a basic compound in the form of a 0.1 to 1 molar aqueous solution are added per 100 parts by weight of waste acetic acid;
e) the first stage is carried out at a temperature of 100° to 118° C. in a period of time of 1 to 4 hours;
f) the complex-forming metal having a large surface area is used in the form of wire, granules or powder;
g) the first runnings of the distillation are withdrawn as an azeotrope together with an added entrainer.

The invention is described in more detail by means of the example:

EXAMPLE 5 kg (81.1 mol) of waste acetic acid from pharmaceutical production, which contains the chlorine-containing impurities acetyl chloride, hydrogen chloride and monochloroacetic acid and also the nitrogen-containing impurities N-methylacetamide, N,N-dimethylacetamide and cyanoacetic acid, were refluxed with 0.19 mol of $Cu(CH_3COO)_2 \cdot H_2O$ and 0.5 l of 0.7 molar sodium hydroxide solution for 3 hours. In an azeotropic distillation, in a column equipped with 40 bubble cap trays, using ethyl acetate as entrainer, water and also low-boiling impurities were separated off as first runnings. 4.5 kg of pure acetic acid were then taken from the column as overhead product.

The quality characteristics of the waste acetic acid, the acetic acid purified according to the invention and industrially pure acetic acid are compared in the table.

TABLE

|  |  | Industrially pure acetic acid | waste acetic acid | purified acetic acid |
|---|---|---|---|---|
| Acetic acid content (%) | min. | 99.5 | 97.3 | 99.9 |
| Water content (%) | max. | 0.1 | 2.2 | 0.02 |
| Residue on evaporation (mg/kg) |  | <30 | 2900 | <5 |
| Solidification temperature (°C.) |  | >16.2 | 13.5 | 16.5 |
| Hazen colour value (APHA) [Color specification according to ASTM] | max. | 10 | 100 | <5 |
| $KMnO_4$ test (min) |  | >15 | <1 | >180 |
| Formic acid (mg/kg) |  | 500 | <100 | <100 |
| Acetaldehyde (mg/kg) | max. | 200 | 8 | 0.2 |
| Heavy metals (mg/kg) | max. | 21 | <2 | <2 |
| Total halogen (mg/kg) |  | <2 | 240 | <2 |
| Total nitrogen (mg/kg) |  | <2 | 430 | <2 |

For the $KMnO_4$ test, 1.0 ml of a 0.1 percent by weight (1 g of $KMnO_4$/l of $H_2O$) $KMnO_4$ solution is diluted with 10 ml of water and 5 ml of acetic acid are added. The time up to decolorization is measured.

We claim:
1. A process for removing nitrogen compounds and halogen compounds from waste acetic acid which comprises adding to said waste acetic acid copper metal or a copper compound selected from the group consisting of copper acetates, copper oxides and copper hydroxides, and an alkali compound selected from the group consisting of sodium hydroxide, sodium carbonate, sodium hydrogen carbonate and sodium acetate, and keeping the resultant mixture at a temperature between 25° and 118° C. over a period of time of 1 to 6 hours in a first distillation stage, and thereafter distilling in a further distillation stage the acetic acid from the thus treated mixture, to separate the nitrogen compounds and halogen compounds.

* * * * *